United States Patent [19]

Sancoff

[11] Patent Number: 5,083,741
[45] Date of Patent: Jan. 28, 1992

[54] IV TUBE CLAMP WITH EXTENDED CLAMPING SURFACE

[75] Inventor: Gregory E. Sancoff, Leucadia, Calif.

[73] Assignee: Block Medical, Inc., Carlsbad, Calif.

[21] Appl. No.: 698,110

[22] Filed: May 10, 1991

[51] Int. Cl.$^5$ .............................................. F16K 7/06
[52] U.S. Cl. ........................................ 251/9; 251/4;
24/557; 24/17 B
[58] Field of Search .............. 251/4, 6, 7, 9, 10;
24/487, 557, 17 B; 128/912

[56] References Cited

U.S. PATENT DOCUMENTS

| | | | |
|---|---|---|---|
| 3,875,619 | 4/1975 | Fortsch | 24/487 X |
| 3,942,228 | 3/1976 | Buckman et al. | 251/4 |
| 4,611,785 | 9/1986 | Steer | 251/4 |
| 4,634,421 | 1/1987 | Hegemann | 251/9 X |

FOREIGN PATENT DOCUMENTS 613394  1/1961  Canada .................. 251/9 X

Primary Examiner—Martin P. Schwadron
Assistant Examiner—Kevin L. Lee
Attorney, Agent, or Firm—Baker, Maxham, Jester & Meador

[57] ABSTRACT

A unitarily constructed clamp for selectively occluding a resilient tube includes a curved platen formed with a pair of holes through which the tube is threaded to position and hold the tube against the concave surface of the platen. The platen has a first end and a second end. Additionally, an articulated pressure member having a hinged juncture is pivotally connected to both the first end and the second end of the platen to locate the juncture between the ends of the platen. With this configuration, the articulated pressure member is positioned for movement between an open configuration and a closed configuration. In the open configuration, the pressure member is distanced from the platen to leave the tube patent. In the closed configuration, the tube is squeezed between the platen and the pressure member to occlude the tube.

20 Claims, 1 Drawing Sheet

5,083,741

IV TUBE CLAMP WITH EXTENDED CLAMPING SURFACE

FIELD OF THE INVENTION

The present invention pertains genera apparatus which clamp onto resilient tubing to occlude the tubing and prevent fluid flow therethrough. More particularly, the present invention pertains to clamps that are useful to occlude tubing which is incorporated into IV administration sets. The present invention is particularly, but not exclusively, useful for occluding IV tubing in situations where either an ON (fluid flow) or an OFF (no fluid flow) condition is desired.

BACKGROUND OF THE INVENTION

Mechanical clamps which can be manipulated to occlude resilient tubing, and thereby prevent fluid flow through the tubing, are known to be useful for various situations. For instance, such a clamp may be helpful in situations wherein fluid is to be transferred from one location to another. Often it is sufficient for the clamping mechanism to simply operate in either an ON condition (i.e. there is fluid flow through the tubing), or an OFF condition (i.e. the tube is occluded and fluid is prevented from flowing through the tube). The situation of particular interest here involves the transfer of medicaments through a specialized device which is commonly referred to as an IV administration set.

Several types of clamps are known to be generally suitable for occluding resilient tubing. For example, a roller clamp having a roller that is positioned for movement along an inclined ramp to progressively squeeze the resilient tube between a platen and the roller is a well known and widely used clamping device. One advantage of the roller clamp is that, in addition to completely occluding the tube, the roller can be positioned to only partially occlude the tube. Thus, some degree of control over the rate of fluid flow through the tube can be obtained by manipulation of the clamp. Roller clamps, however, are very susceptible to creep and, consequently, they must be frequently monitored to ensure they are properly clamping the tube. Further, the point of occlusion where the tube is squeezed between the roller and the platen is relatively small. This rather confined area of restriction has the unfortunate tendency to cause the tube to take a permanent set and not return to its original configuration when the clamp is released. The result can be an unwanted restriction which permanently alters the flow of fluid through the tube.

Another type IV tubing clamp is a pincers-type clamp which basically includes two surfaces that are brought together to clamp the tube between the surfaces. This type clamp, unlike a roller clamp, does not typically have an adjustable capability by which the flow of fluid through the tube can be controlled. Like roller clamps, however, the pincers-type clamps have a tendency to cause an unwanted set in the pinched tube. Also, to whatever extent the surfaces of the pincers-type clamp can move relative to each other, there can be significant creep with a consequent compromise of the occlusion.

Regardless of the particular type clamp which is used for occluding a resilient tube, it is important to have some visual indication that the clamp is in an effective clamping configuration. Also, and equally as important, it is desirable that there be some easy visualization of the condition when the clamp is not effectively occluding the tube.

In light of the above, it is an object of the present invention to provide an IV tubing clamp which gives an obvious visualization of the ON and OFF configuration of the clamp. Another object of the present invention is to provide an IV tubing clamp which establishes a zone of occlusion over an extended area of the tubing to minimize or avoid a permanent set in the tube after the clamp is released. Yet another object of the present invention is to provide an IV tubing clamp which has imperceptible, if any, creep in the location of the occlusion on the tubing. Still another object of the present invention is to provide an IV tubing clamp which is useful for occluding IV tubings having various outer diameter dimensions. Another object of the present invention is to provide an IV tubing clamp which is simple to use, relatively easy to manufacture, and comparatively cost effective.

SUMMARY OF THE INVENTION

An ON-OFF clamp of unitary construction for occluding a resilient IV tube includes a concave platen which is formed with a pair of holes to threadingly receive the tube through the holes and position the tube against the platen. An articulated pressure member is operatively attached to the platen for movement between an open configuration wherein the pressure member is distanced from the platen to leave the tube patent (an ON condition), and a closed configuration wherein the tube is squeezed between the platen and the pressure member to occlude the tube (an OFF condition). Specifically, the pressure member includes a first segment which is attached to a second segment at a juncture by an integral hinge. The first segment is pivotally attached to a first end of the platen and the second segment is pivotally attached to a second end of the platen to position the juncture at approximately the midpoint between the ends of the platen.

For the clamp of the present invention, the curved platen is relatively resilient so that as the pressure member is moved, the platen reacts to snappingly hold the pressure member in its open configuration or in its closed configuration for engagement with the tube. Further, the first segment is formed with a detent and the second segment is formed with a latch which are engageable with each other to hold the articulated pressure member in its closed configuration.

In the closed configuration, the integral hinge at the juncture between the first pressure segment and the second pressure segment creates a pressure point which urges against the tube to help establish the occlusion. This pressure point also helps in gripping the tube to prevent or minimize any creep in the clamping action of the ON-OFF clamp.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENT

Figure 1:
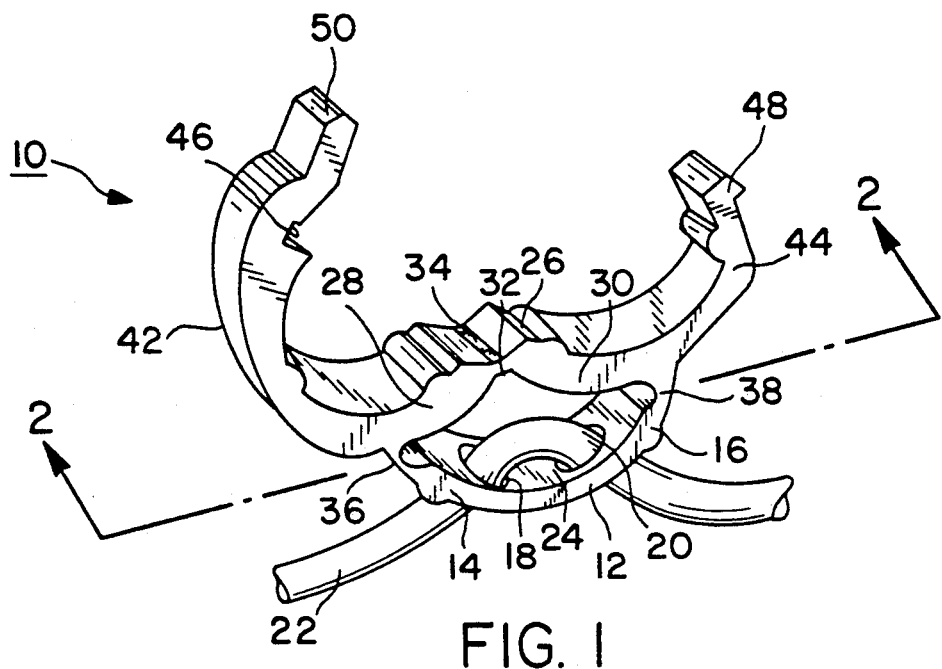
FIG. 1 is a perspective view of the IV tube clamp of the present invention shown in its open configuration and engaged with an IV tube.

Referring initially to FIG. 1, the ON-OFF clamp for occluding a resilient tubing is shown and generally designated 10. As shown, the clamp 10 includes a platen 12 which is curved along the length between its first end 14 and its second end 16. A hole 18 is formed through the platen 12 near its first end 14, and another hole 20 is formed through the platen 12 near its second end 16. An IV tube 22 can then be threaded through the holes 18 and 20 to position and hold the tube 22 against the concave surface 24 of platen 12. It will be appreciated that the holes 18 and 20 can be of sufficient size to hold IV tubes 22 of various sizes.

The tube clamp 10 also includes an articulated pressure member 26 that has a first pressure segment 28 and a second pressure segment 30. As shown in FIG. 1, the first pressure segment 28 is hingedly joined to the second pressure segment 30 at their juncture 32 by an integral hinge 34. The integral hinge 34 is of a type well known in the pertinent art and commonly referred to as a "living hinge". Further, as shown, the first pressure segment 28 is pivotally attached to the first end 14 of platen 12 by an integral hinge 36. Similarly, the second pressure segment 30 is pivotally attached to the second end 16 of the platen 12 by an integral hinge 38. The integral hinges 34, 36 and 38 are all constructed in essentially the same manner. Importantly, they are each operationally functional because the clamp 10 is of unitary construction and is made of a plastic, or other suitable material, which is resilient and bendable at points of reduced cross section such as are established for the hinges 34, 36 and 38.

Figure 2:
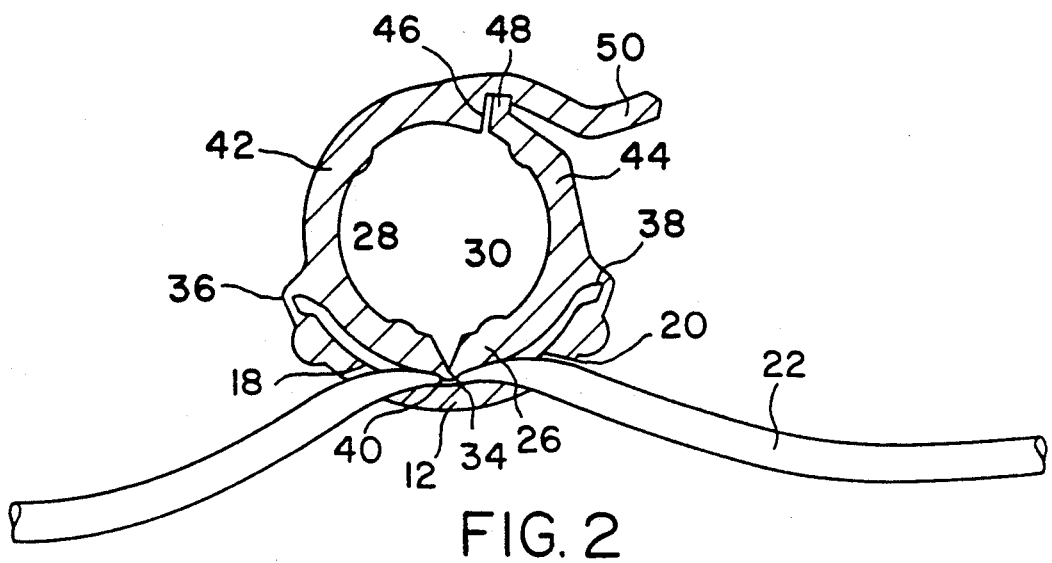
FIG. 2 is a cross-sectional view of the IV clamp in its closed configuration and shown in combination with an IV tube as would be seen along the line 2—2 in FIG. 1.

With the combination as disclosed above, the clamp 10 is operable to move the pressure member 26 between an open configuration or ON condition (shown in FIG. 1) and a closed configuration or OFF condition (shown in FIG. 2). As intended for the present invention, when the articulated pressure member 26 is in the open configuration, the pressure member 26 is distanced from the platen 12 to leave the tube 22 patent and allow fluid to flow therethrough. On the other hand, when the articulated pressure member 26 is in its closed configuration, the pressure member 26 urges against the tube 22 to squeeze the tube 22 between the pressure member 26 and the platen 12. Consequently, when clamp 10 is in the closed configuration, a zone of occlusion is formed on the tube 22 which prevents fluid from flowing through the tube 22.

FIG. 2 also shows that when clamp 10 and the articulated pressure member 26 are placed into the closed configuration, the integral hinge 34 creates a contact point 40 which urges against the tube 22. As intended for the present invention, the contact point 40 helps grip the tube 22 to prevent any creep from occurring between the clamp 10 and the tube 22.

In both FIG. 1 and 2, it will be appreciated that the clamp 10 also includes an arm 42 which is a continuing extension of the first pressure segment 28. Also, clamp 10 includes an arm 44 which is a continuing extension of the second pressure segment 30. A detent 46 is formed on the arm 42, and a latch 48 is formed on the arm 44. As best seen in FIG. 2, the latch 48 is engageable with the detent 46 to hold the clamp 10 and the articulated pressure member 26 in the closed configuration. Further, arm 42 is shown formed with an activator tab 50 which can be easily manipulated by the operator to move clamp 10 between its open configuration and its closed configuration.

As implied above, the clamp 10 is preferably made of a plastic material. Importantly, whatever material is used for the construction of clamp 10, it must have some resilience. This is so in order to allow the clamp 10 to be manipulated between the open and the closed configurations. Specifically, the platen 12 is curved or bowed to allow a bending of the platen 12. As will be appreciated by the skilled artisan, this bending of the platen 12 will either distance the ends 14 and 16 from each other or bring them closer together. From the bent condition, the platen 12 will then tend to return to its original unstressed condition. With this ability of the platen 12 to be resiliently bent, the pressure segments 28 and 30 are able to pivot respectively about the ends 14 and 16 of the platen 12 due to a temporary distancing of the ends 14 and 16 from each other. It happens, due to the resiliency and reaction of the platen 12, that there is a slight snapping movement of the pressure member 26 as it moves between the open and the closed configuration. Thus, there is a tendency for the articulated pressure member 26 to remain in a particular configuration after the clamp 10 is moved into that configuration. This helps maintain an occlusion on the tube 22 when the clamp 10 is in the closed configuration, and helps keep the arms 42 and 44 separated from each other when the clamp is in the open configuration. Importantly, it is the resultant obviousness of the separated arms 42 and 44 when clamp 10 is in the open configuration that provides an easy visual indication of the open condition of the clamp 10.

While the particular IV tube clamp as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A resilient tube clamp which comprises:
   a platen for holding said tube, said platen having a first end and a second end; and
   an articulated pressure member pivotally connected to said first end and said second end of said platen for movement between an open configuration wherein said pressure member is distanced from said platen to leave said tube patent, and a closed configuration wherein said tube is squeezed between said platen and said pressure member to occlude said tube.

2. A clamp as recited in claim 1 wherein said platen is formed with a pair of holes to threadingly receive said tube therethrough to position and hold said tube against said platen.

3. A clamp as recited in claim 1 wherein said articulated pressure member comprises a first pressure segment pivotally attached to a second pressure segment, and wherein said first pressure segment is pivotally attached to said first end of said platen and said second pressure segment is pivotally attached to said second end of said platen.

4. A clamp as recited in claim 3 wherein said first and second pressure segments are relatively rigid, and said platen is curved and relatively resilient to snappingly hold said articulated pressure member in said closed configuration.

5. A clamp as recited in claim 3 wherein said first pressure segment is formed with a detent and said second pressure segment is formed with a latch engageable with said detent to hold said articulated pressure member in said closed configuration.

6. A clamp as recited in claim 3 further comprising an integral hinge for attaching said first pressure segment to said second pressure segment, and wherein said integral hinge creates a pressure point for urging against said tube when said articulated pressure member is in said closed configuration.

7. A clamp as recited in claim 6 further comprising an integral hinge for attaching said first pressure member to said first end of said platen, and an integral hinge for attaching said second pressure member to said second end of said platen.

8. A clamp as recited in claim 6 wherein said pressure point is created substantially midway between said first end and said second end of said platen.

9. A clamp as recited in claim 7 wherein said clamp is unitary and is made of plastic.

10. A clamp for occluding a resilient tube which comprises:
a curved platen for holding said tube;
a first pressure segment pivotally mounted on said platen; and
a second pressure segment pivotally mounted on said platen, said second pressure segment being hingedly attached to said first pressure segment to establish an articulated pressure member therewith, said articulated pressure member being moveable relative to said platen between an open configuration wherein said pressure member is distanced from said platen to leave said tube patent, and a closed configuration wherein said tube is squeezed between said platen and said pressure member to occlude said tube.

11. A clamp as recited in claim 10 wherein said platen has a first end and a second end, and said first pressure segment is attached to said first end with an integral hinge, and said second pressure segment is attached to said second end with an integral hinge.

12. A clamp as recited in claim 11 said first pressure segment is attached to said second pressure segment at a juncture substantially midway between said first end and said second end of said platen.

13. A clamp as recited in claim 12 wherein said platen is formed with a pair of holes to threadingly receive said tube therethrough to position and hold said tube against said platen.

14. A clamp as recited in claim 13 wherein said first and second pressure segments are relatively rigid, and said platen is relatively resilient to snappingly hold said articulated pressure member in said closed configuration.

15. A clamp as recited in claim 13 wherein said first pressure segment is formed with a detent and said second pressure is formed with a latch engageable with said detent to hold said articulated pressure member in said closed configuration.

16. A clamp as recited in claim 13 wherein said integral hinge between said first pressure segment and said second pressure segment creates a pressure point for urging against said tube when said articulated pressure member is in said closed configuration.

17. A clamp as recited in claim 14 wherein said clamp is unitary and is made of plastic.

18. A method for occluding a resilient IV tube which comprises the steps of:
providing a unitarily constructed clamp having a platen formed with a pair of holes to threadingly receive said tube therethrough to position and hold said tube against said platen, said platen having a first end and a second end, said clamp further having an articulated pressure member pivotally connected to said first end and said second end of said platen for movement between an open configuration wherein said pressure member is distanced from said platen to leave said tube patent, and a closed configuration wherein said tube is squeezed between said platen and said pressure member to occlude said tube;
positioning said tube through said holes in said platen to position said tube against said platen; and
selectively manipulating said clamp between said open configuration and said closed configuration.

19. A method as recited in claim 18 wherein said articulated pressure member comprises a first pressure segment pivotally attached to a second pressure segment, and wherein said first pressure segment is pivotally attached to said first end of said platen and said second pressure segment is pivotally attached to said second end of said platen.

20. A method as recited in claim 19 wherein said clamp further comprises an integral hinge for attaching said first pressure segment to said second pressure segment, and wherein said integral hinge creates a pressure point for urging against said tube when said articulated pressure member is in said closed configuration.

* * * * *